United States Patent [19]
Miyake

[11] Patent Number: 5,629,747
[45] Date of Patent: May 13, 1997

[54] HAND-HELD OPHTHALMOLOGICAL APPARATUS HAVING A RETRACTABLE FOREHEAD CONTACT MEMBER

[75] Inventor: Nobuyuki Miyake, Yokohama, Japan

[73] Assignee: Nikon Corporation, Tokyo, Japan

[21] Appl. No.: 566,912

[22] Filed: Dec. 4, 1995

[30] Foreign Application Priority Data

Dec. 12, 1994 [JP] Japan .................................. 6-307928

[51] Int. Cl.⁶ .............................. A61B 3/10; A61B 3/00
[52] U.S. Cl. .............................. 351/218; 351/245
[58] Field of Search .................................. 351/200, 218, 351/245

[56] References Cited

U.S. PATENT DOCUMENTS 4,461,551  7/1984  Blaha .................................. 351/214

*Primary Examiner*—Huy Mai
*Attorney, Agent, or Firm*—Shapiro and Shapiro

[57] ABSTRACT

A hand-held ophthalmological apparatus comprises a measuring unit for measuring an examinee's eye, a hand unit attached to the measuring unit and held by a measurer and a forehead contact member for contacting a forehead of the examinee. The apparatus maintains a relative positional relationship between the measuring unit and the examinee's eye during a measurement.

5 Claims, 5 Drawing Sheets

HAND-HELD OPHTHALMOLOGICAL APPARATUS HAVING A RETRACTABLE FOREHEAD CONTACT MEMBER

BACKGROUND OF THE INVENTION

1. Field of the Invention

The present invention relates to a hand-held ophthalmological apparatus, including a hand unit held by a measurer, for observing or measuring an examinee's eye.

2. Related Background Art

As illustrated in FIG. 6, e.g., a tabletop eye refracting power measuring apparatus may be considered conventional ophthalmological apparatus.

This eye refracting power measuring apparatus is constructed of a base 8 and a slide pedestal 6 so mounted as to be movable in back-and-forth/right-and-left directions with respect to this base 8. This measuring apparatus is also constructed of a measuring unit 5 equipped with a variety of optical members and so mounted as to be movable in up-and-down directions with respect to the slide pedestal 6 and a support unit 9 for supporting the head of an examinee 1. The support unit 9 has a forehead contact member 9a, a jaw supporter 9b and a support rod 9c through which these components are linked to the base 8.

In the case of using this eye refracting power measuring apparatus, at first, a jaw of the examinee 1 is placed on the jaw supporter 9b, and a forehead 3 of the examinee 1 is brought into contact with the forehead contact member 9a. Then, the head of the examinee 1 is fixed with respect to the base 8. Subsequently, the measuring unit 5 is moved by operating an operation handle 7 provided on the slide pedestal 6 so that an optical axis C of the measuring unit 5 is set coaxial with an optical axis of the examinee's eye 2. Thereafter, the measurer makes a predetermined measurement while seeing through the optical system or watching a monitor.

A small-sized hand-held eye refracting power measuring apparatus has been offered in recent years in response to a demand for measuring the eye refracting power during a variety of operations. This eye refracting power measuring apparatus includes a measuring optical system for one eye and a hand unit fixed thereto. This type of hand-held eye refracting power measuring apparatus unlike the tabletop type, is not provided with the base, the slide pedestal and the support unit to allow it to be portable in order to examine the examinee's eye in every state as in the case of, e.g., an operation or the like.

According to such a conventional hand-held ophthalmological apparatus, however, as explained above, the measurer having this apparatus is incapable of maintaining a mutual positional relationship between the examinee's eye and the measuring unit during the measurement as a result of emphasizing the portability, resulting in such a problem that a satisfactory measurement can not be performed.

SUMMARY OF THE INVENTION

It is a primary object of the present invention to provide a hand-held ophthalmological apparatus capable of continuously keeping a relative positional relationship between an examinee's eye and a measuring unit without causing a decline in terms of its portability.

To accomplish the above object, according to one aspect of the present invention, a hand-held ophthalmological apparatus comprises a measuring unit for measuring an eye of an examinee, a hand unit attached to the measuring unit and held by a measurer and a forehead contact member brought into contact with a forehead of the examinee.

Further, the object given above can be also accomplished by the following construction. The hand-held ophthalmological apparatus comprises the forehead contact for contacting the forehead of the examinee and the measuring unit formed with a housing portion capable of housing the forehead contact member in a position above an optical axis of the measuring unit but on the side of the examinee in a using state thereof. The same apparatus further comprises a moving mechanism for movably supporting the forehead contact member in a direction parallel to the optical axis between a housing position where the forehead contact member is housed and a using position where the forehead contact member is out of the housing position in the direction parallel to the optical axis.

According to the present invention, the forehead contact member is removed from the housing portion and brought into contact with the forehead of the examinee, thereby making it possible to substantially maintain a relative positional relationship between the present apparatus and the examinee during the measurement. It is therefore feasible to perform a stable observation and measurement. Further, during an unused state of the present apparatus, the forehead contact member can be housed in the housing portion of the measuring unit, and, hence, the portability is not adversely affected.

BRIEF DESCRIPTION OF THE DRAWINGS

Other objects and advantages of the present invention will become apparent during the following discussion in conjunction with the accompanying drawings, in which.

DESCRIPTION OF THE PREFERRED EMBODIMENT

One embodiment of a hand-held ophthalmological apparatus according to the present invention will be discussed with reference to FIGS. 1 to 5.

Figure 1:
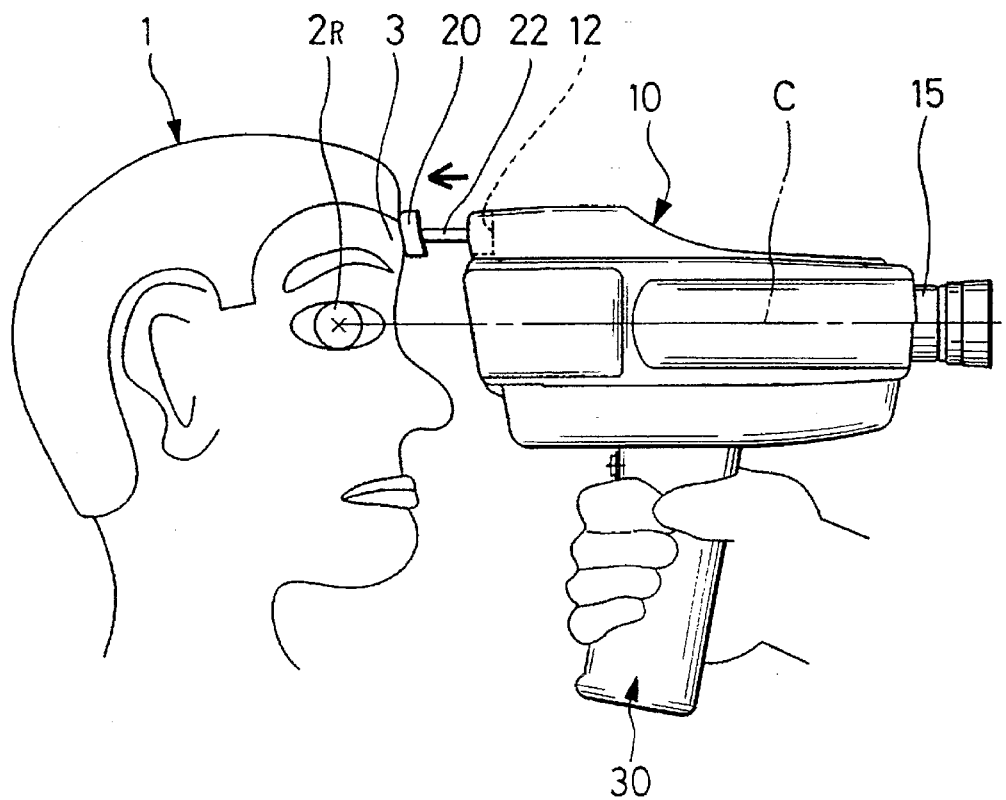
FIG. 1 is a side view illustrating a hand-held eye refracting power measuring apparatus when used in one embodiment of the present invention.
Figure 2:
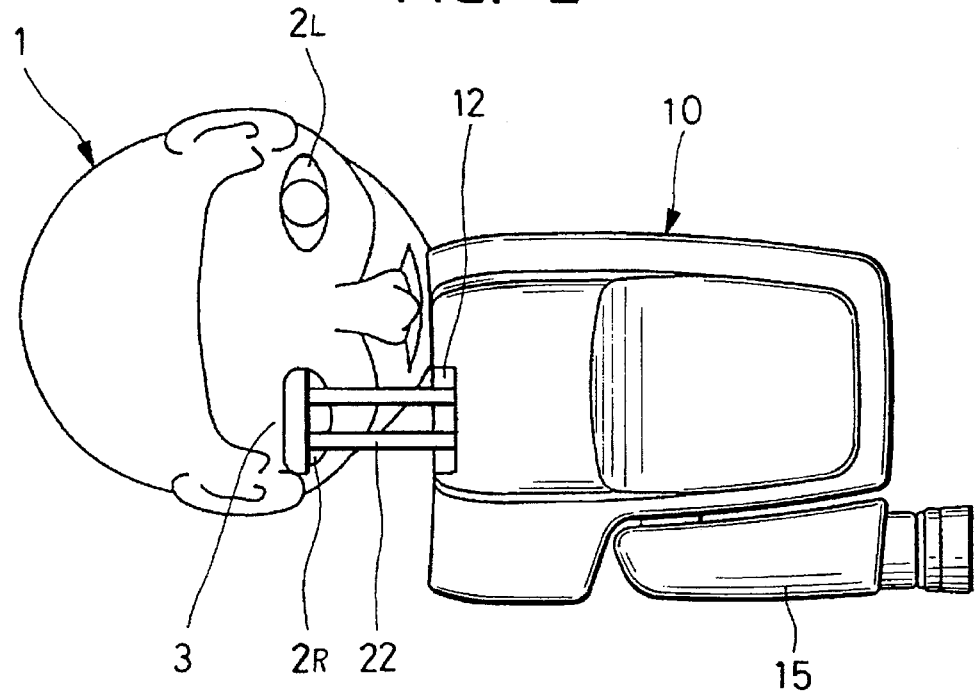
FIG. 2 is a top view illustrating the hand-held eye refracting power measuring apparatus when used in one embodiment of the present invention.

The ophthalmological apparatus in this embodiment as illustrated in FIGS. 1 and 2, defined as an eye refracting power measuring apparatus including a hand unit 30 held by a measurer.

Figure 4:
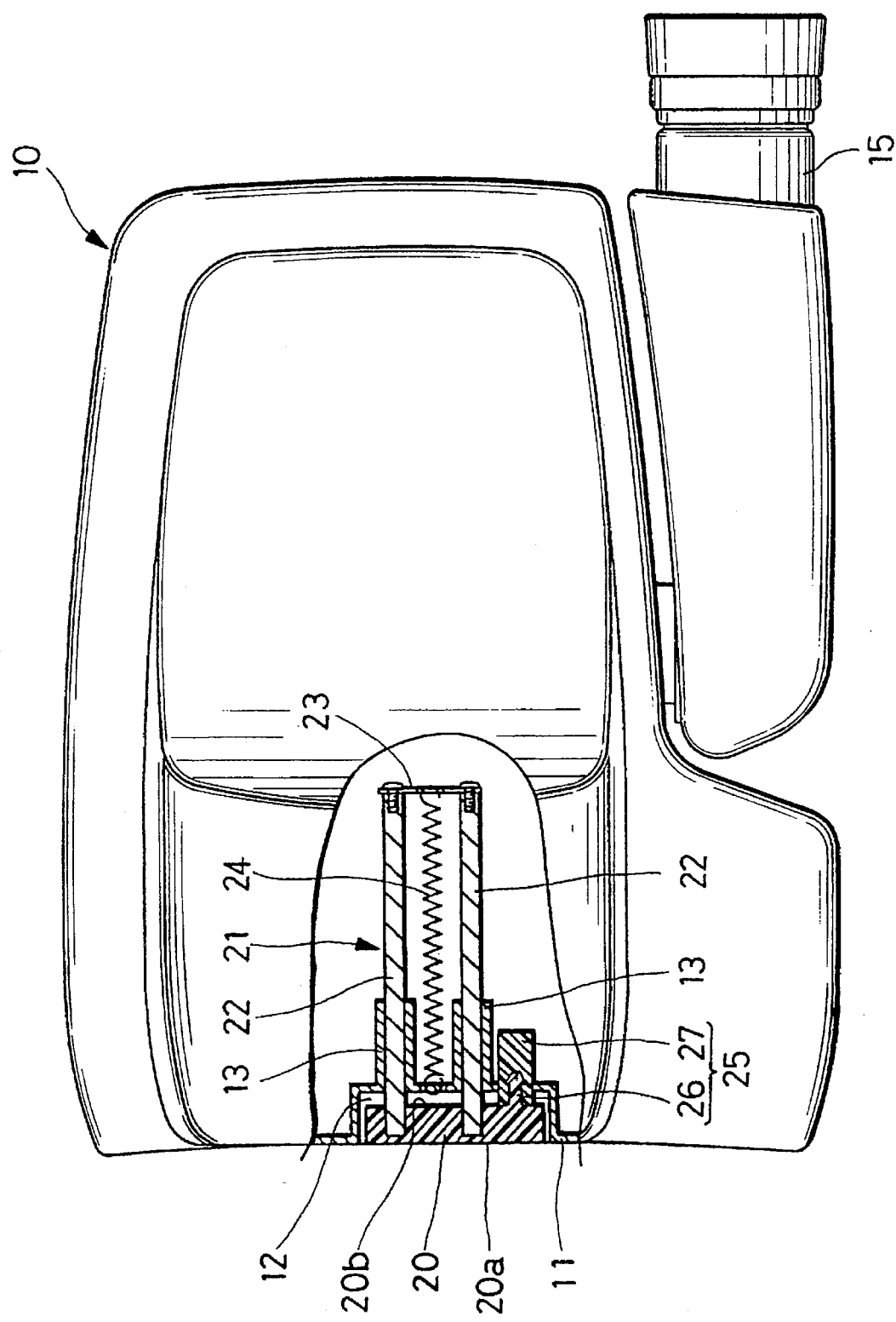
FIG. 4 is a cut-away top view (showing the housing state) of the principal portion of the measuring unit of the hand-held eye refracting power measuring apparatus in one embodiment of the present invention.

This hand-held eye refracting power measuring apparatus is constructed of, as shown in FIGS. 1 and 4, a measuring unit 10 having a measuring optical system (unillustrated) for one eye, the hand unit 30 fixed to a lower portion of this measuring unit 10, a forehead contact member 20 for contact with a forehead 3 of an examinee 1 and a forehead contact member moving mechanism 21 for movably supporting this forehead contact member.

Figure 5:
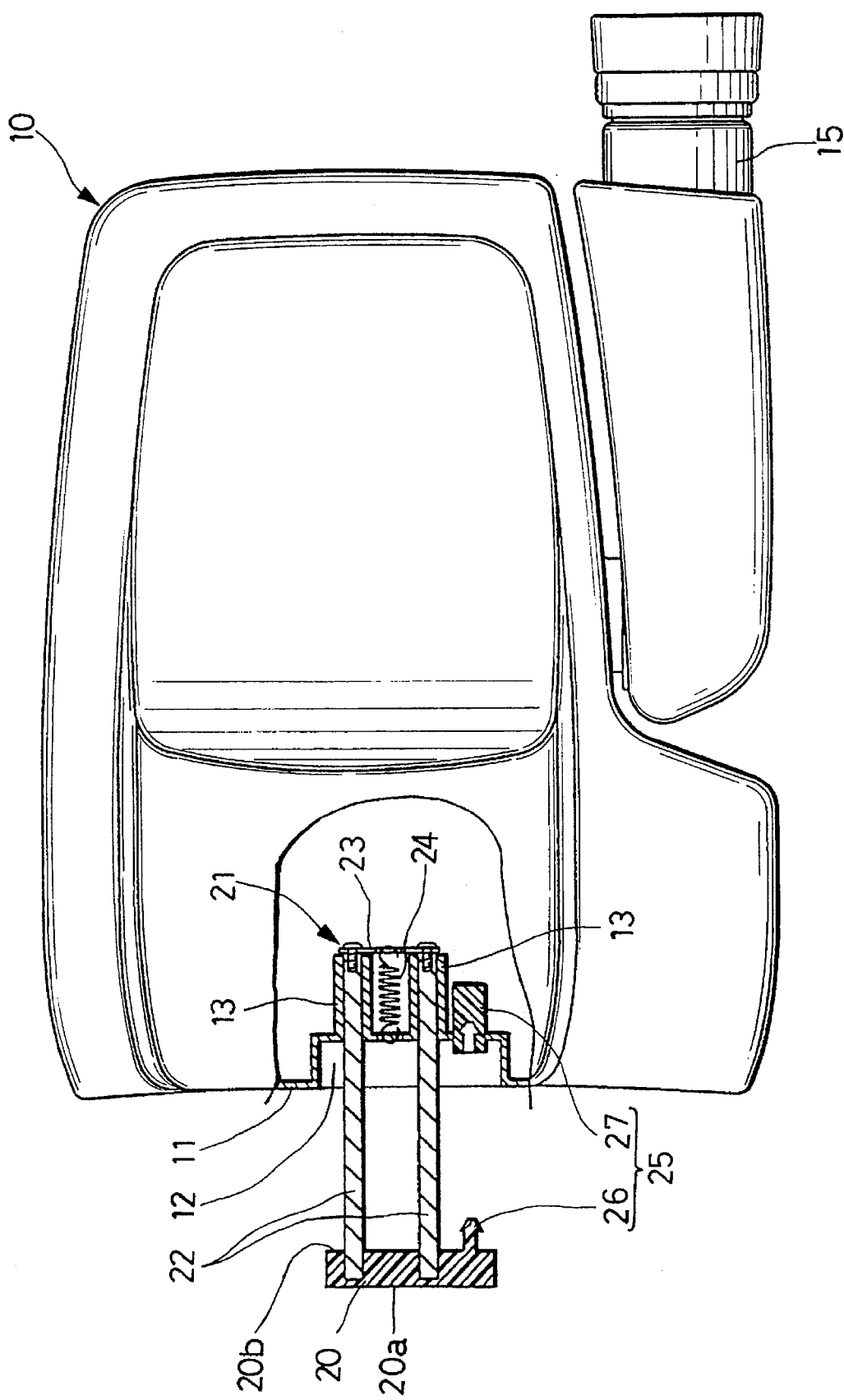
FIG. 5 is a cut-away top view (showing a using state) of the principal portion of the measuring unit of the hand-held eye refracting power measuring apparatus in one embodiment of the present invention.
Figure 6:
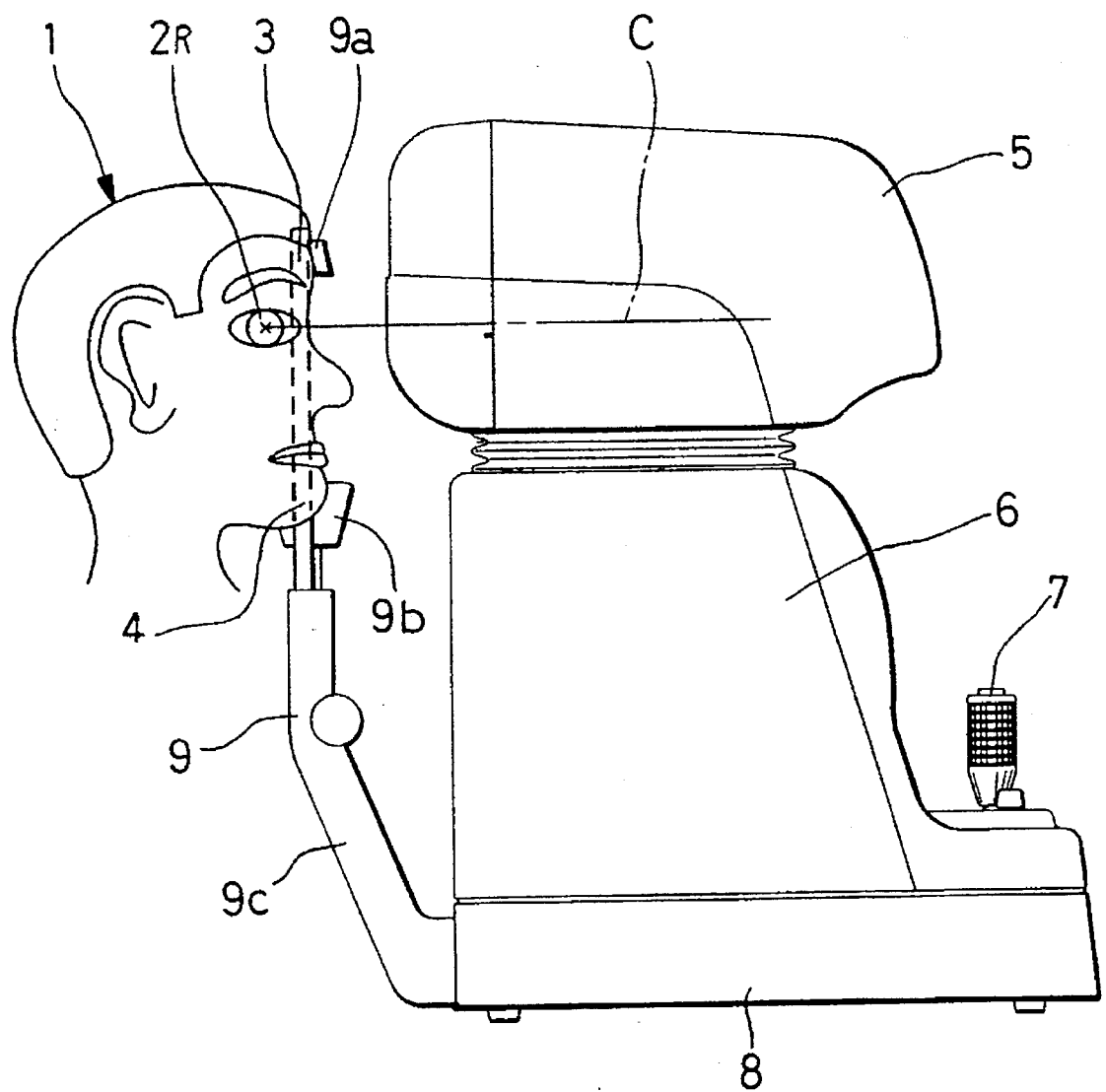
FIG. 6 is a side view illustrating a tabletop eye refracting power measuring apparatus.

The measuring unit 10 includes a measuring optical system composed of a plurality of optical elements such as lenses and a casing 11 for covering this measuring optical system. The casing 11 of this measuring unit 10 is, as illustrated in FIGS. 3 to 5, formed with a recessed housing portion 12 capable of housing the forehead contact member 20 in a position above an optical axis C of the measuring optical system but on the side of the examinee in a using state.

The forehead contact member moving mechanism 21 has two lengths of slide rods 22, 22 parallel to each other, each having an edge fixed to a rear surface (opposite to a surface 20a contacting the forehead) 20b of the forehead contact member 20. This moving mechanism 21 also has guide members 13, 13 for movably supporting these slide rods 22, 22 in a direction parallel to the optical axis C of the measuring optical system, a spring (forehead contact member biasing member) 24 for biasing the forehead contact member 20 in such a direction as to be ejected out of the housing portion 12 and a forehead holding mechanism 25 for holding the forehead contact member 20 in the housing portion 12. The other ends of the two slide rods 22, 22 are connected to each other via a connecting plate 23. One end of the spring 24 is secured to a bottom of the housing portion 12, while the other end thereof is secured to the connecting plate 23. The forehead contact member holding mechanism 25 is, as illustrated in FIG. 5, constructed of a head-tapered pin 26 fixed to the rear surface 20b of the forehead contact member 20 but extending in the direction parallel to the optical axis C and a pin insertion member 27 into which the head-tapered pin 26 can be inserted. This head-tapered pin 26 and the pin insertion member 27 are each formed of a resin. Even when the head-tapered pin 26 is inserted into the pin insertion member 27, upon applying a pull-out force to the head-tapered pin 26, the head-tapered pin 26 can be pulled out of the pin insertion member 27 owing to an elastic deformation of the resin.

Given next is an explanation of a method of operating the hand-held eye refracting power measuring apparatus in accordance with this embodiment.

Figure 3:
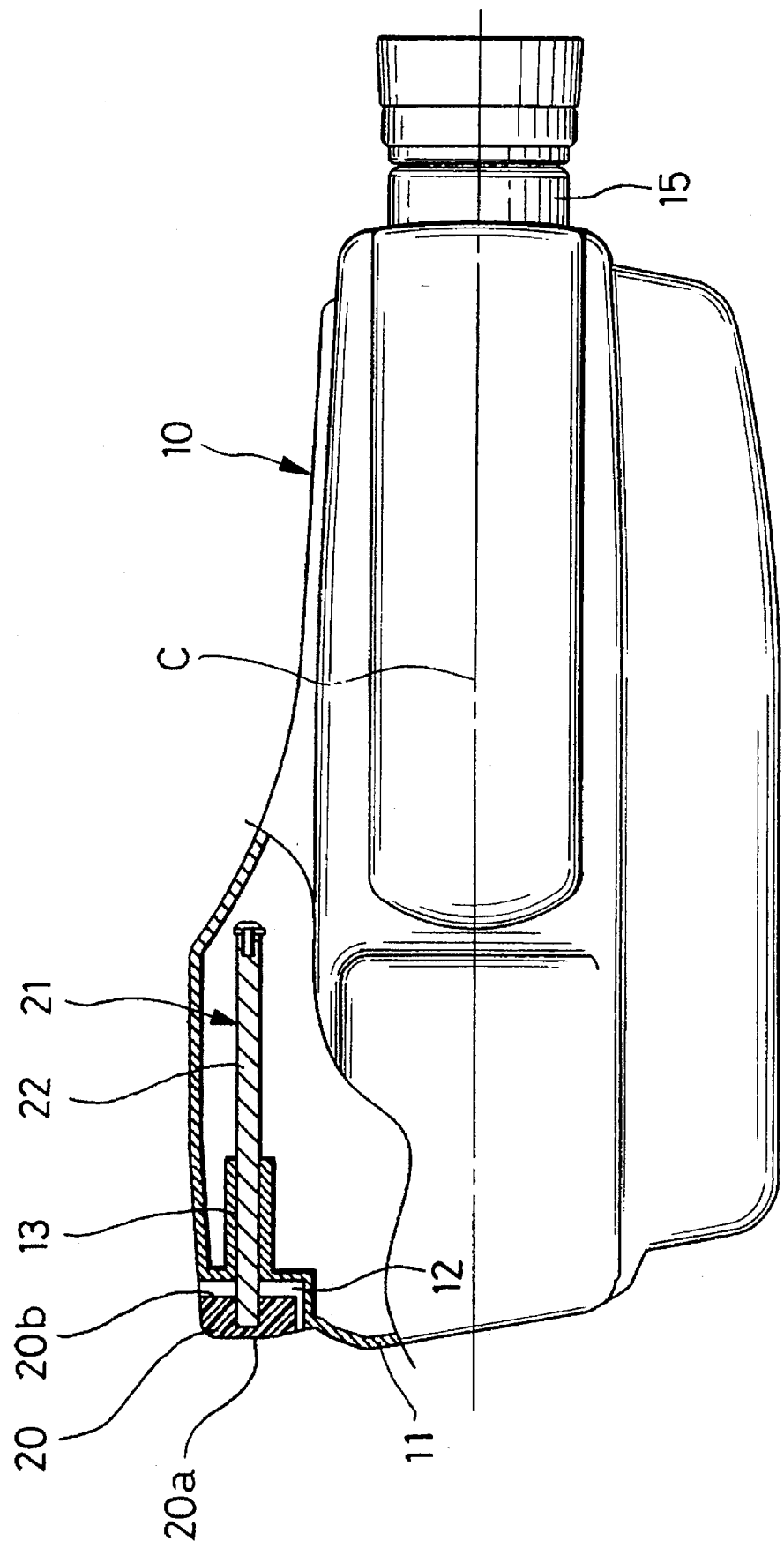
FIG. 3 is a cut-away side view (showing a housing state) of the principal portion of a measuring unit of the hand-held eye refracting measuring apparatus in one embodiment of the present invention.

When this eye refracting power measuring apparatus is not used, as illustrated in FIGS. 3 and 4, the forehead contact member 20 is housed in the housing portion 12 of the measuring unit 10. At this time, the head-tapered pin 26 of the forehead contact member holding mechanism 25 is inserted into the pin insertion member 27, while the spring 24 remains stretched.

When using the eye refracting power measuring apparatus, a slight force acting to exit the housing portion 12 is applied to the forehead contact member 20 housed in the housing portion 12. Hereupon, the head-tapered pin 26 of the forehead contact member holding mechanism 25 is removed from the pin insertion member 27. In consequence of this, as depicted in FIG. 5, the spring 24 remaining stretched acts to contract, with the result that the forehead contact member 20 is ejected out of the housing portion 12. The forehead contact member 20, when the connecting plate 23 impinges on the guide member 13, stops there. Next, as illustrated in FIGS. 1 and 2, the forehead contact member 20 is brought into contact with the forehead 3 of the examinee 1 by moving the present apparatus back and forth, right and left and up and down with respect to the examinee 1 while holding the hand unit 30 so that the optical axis of the examinee's eye 2 is substantially coaxial with the optical axis C of the measuring optical system. Subsequently, the present apparatus is moved up and down and right and left with respect to the examinee 1 while seeing through a viewfinder 15 constituting part of the measuring optical system, thereby finally making the optical axis of the examinee's eye 2 coaxial with the optical axis C of the measuring optical system. Then, the present apparatus is moved to and fro with respect to the examinee 1, thereby adjusting a focal point of the measuring optical system to the examinee's eye 2. Subsequently, in this state, the refracting power of the examinee's eye 2 is measured.

Thus, the relative positional relationship between the examinee 1 and the present apparatus during the measurement can be, though not so accurate as the tabletop measuring apparatus, maintained by applying the forehead contact member 20 to the forehead 3 of the examinee 1, and, therefore, the measurement can be carried out in a stable state. Further, in accordance with this embodiment, the forehead contact member can be housed in the housing portion 12 of the measuring unit 10 during an unused state of the apparatus, and hence the portability thereof does not decline. By the way, the above description has been given on the premise that the forehead contact member 20 is, when using the present apparatus, taken out of the housing portion 12 and then employed. However, if the examinee's eye 2 is in a well-fixed state, and when the relative positional relationship between the examinee 1 and the present apparatus can be comparatively easily maintained, the measurement may be, as a matter of course, performed in an as-housed state of the forehead contact member 20 in the housing portion 12.

Note that the forehead contact member moving mechanism 21 in this embodiment is capable of, when the head-tapered pin 26 is removed from the pin insertion member 27, freely moving the forehead contact member 20 back and forth with respect to the measuring unit 10, but the present invention is not limited to this construction. For example, a rack may be disposed in parallel to the optical axis C of the measuring optical system by use of a rack and a pinion, and the forehead contact member 20 may be movable little by little by rotating the pinion. Further, the forehead contact member holding mechanism 25 in this embodiment makes use of the pin 26. In this connection, however, any kind of forehead contact member 20 may be employed on the condition that it can be temporarily held in the housing portion 12. For instance, a magnet or the like exhibiting a magnetic force slightly larger than the biasing force of the spring 24 may also be used. Moreover, in accordance with this embodiment, the present invention is applied to the eye refracting power measuring apparatus, but the invention also may be applied to an apparatus for simply observing (including photographing) the examinee's eye 2 or performing other measurements.

It is apparent that, in this invention, a wide range of different working modes can be formed based on the invention without deviating from the spirit and scope of the invention. This invention is not restricted by its specific working modes except being limited by the appended claims.

What is claimed is:

1. A hand-held ophthalmological apparatus comprising:
  a measuring unit for measuring a characteristic of an eye of an examines, said measuring unit having a housing portion;

a hand unit, attached to said measuring unit, for being held by an operator;

a forehead contact member for contacting a forehead of the examines, said forehead contact member being supported by a support member that is extendable and retractable relative to said housing portion, and said housing portion having a recessed portion for receiving said forehead contact member when said support member is in a retracted state.

2. A hand-held ophthalmological apparatus according to claim 1, wherein said recessed portion surrounds a substantial portion of said forehead contact member when said forehead contact member is received by said recessed portion.

3. A hand-held ophthalmological apparatus according to claim 1, further comprising a mechanism supported on said housing portion for releasably locking said forehead contact member received by said recessed portion.

4. A hand-held ophthalmological apparatus according to claim 1, further comprising a biasing member for biasing said forehead contact member outwardly from said recessed portion.

5. A hand-held ophthalmological apparatus comprising:

an observing unit for observing an eye of an examinee;

a hand unit, attached to said observing unit, for being held by an operator;

a forehead contact member that is morale relative to said observing unit between an extended position and a retracted position;

a biasing member for biasing said forehead contact member toward the extended position; and a mechanism for automatically, releasably locking said forehead contact member at the retracted position.

* * * * *